(12) United States Patent
Cappiello et al.

(10) Patent No.: US 7,022,103 B2
(45) Date of Patent: Apr. 4, 2006

(54) APPARATUS AND METHOD OF IDENTIFYING RECTOVAGINAL FISTULAS

(76) Inventors: Gerard Cappiello, 1965 Lynwood Ct., Dunedin, FL (US) 34698-2845; Mimi Cappiello, 1965 Lynwood Ct., Dunedin, FL (US) 34698-2845

( * ) Notice: Subject to any disclaimer, the term of this patent is extended or adjusted under 35 U.S.C. 154(b) by 177 days.

(21) Appl. No.: 10/201,742

(22) Filed: Jul. 23, 2002

(65) Prior Publication Data

US 2004/0064017 A1 Apr. 1, 2004

(51) Int. Cl.
*A61M 29/00* (2006.01)

(52) U.S. Cl. .............. 604/102.01; 604/101.03; 604/915; 606/197

(58) Field of Classification Search ............ 604/96.01, 604/101.01–101.05, 102.01–102.03, 915–916, 604/919, 275, 278–279, 104; 606/191–192, 606/197
See application file for complete search history.

(56) References Cited

U.S. PATENT DOCUMENTS

| | | | | |
|---|---|---|---|---|
| 2,687,131 A | * | 8/1954 | Raiche | ................. 604/101.05 |
| 2,936,760 A | * | 5/1960 | Gants | ................... 604/101.03 |
| 4,211,233 A | * | 7/1980 | Lin | ............................. 604/43 |
| 4,432,758 A | * | 2/1984 | Finegold | ................... 604/104 |
| 4,809,710 A | | 3/1989 | Williamson | |
| 5,312,343 A | | 5/1994 | Krog et al. | |
| 5,411,473 A | * | 5/1995 | Ahmed | ............................ 604/8 |
| 5,575,811 A | | 11/1996 | Reid et al. | |
| 6,077,257 A | * | 6/2000 | Edwards et al. | ............. 604/506 |
| 6,488,653 B1 | * | 12/2002 | Lombardo | .............. 604/103.06 |
| 6,706,026 B1 | * | 3/2004 | Goldstein et al. | ........... 604/278 |

* cited by examiner

*Primary Examiner*—LoAn H. Thanh
(74) *Attorney, Agent, or Firm*—Garvey, Smith, Nehrbass & Doody, L.L.C.; Gregory C. Smith

(57) ABSTRACT

An apparatus for locating rectovaginal fistulas, including a cannula of a predetermined length, open-ended on its first end having an inflatable balloon portion on its closed second end; the first end of the cannula further comprising a cone portion along its length to seal up against the exterior wall entrance to the rectum, after the second end of the cannula has been inserted into a patient's rectum; a fluid line is positioned within the cannula space for inflating the balloon after the cannula is in place in the rectum to seal the distal end of the rectum passage; a plurality of openings are provided along the wall of the cannula between the balloon and the cone at the first end of the cannula; a colored gel or other fluid insertable into the cannula to the extent that the gel or other fluid escapes the cannula through the openings and enters the void between the cannula and the wall of the rectum, with sufficient gel or other fluid entering the void so that gel or fluid would seep into any fistulas present and would be visually identifiable in the vagina for treatment.

16 Claims, 4 Drawing Sheets

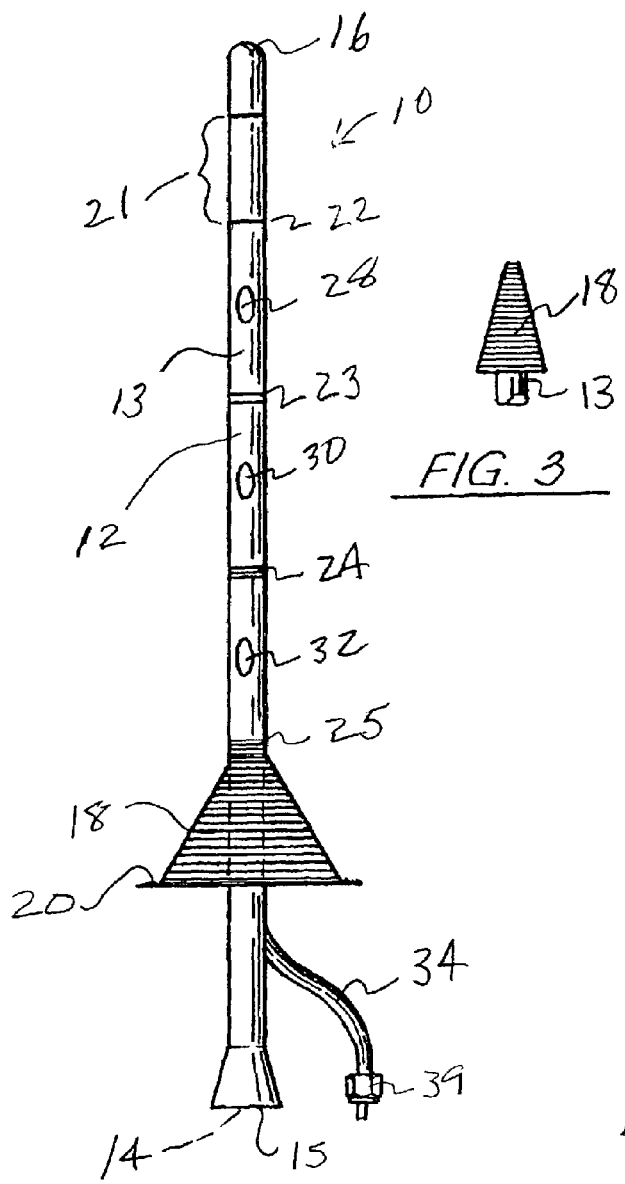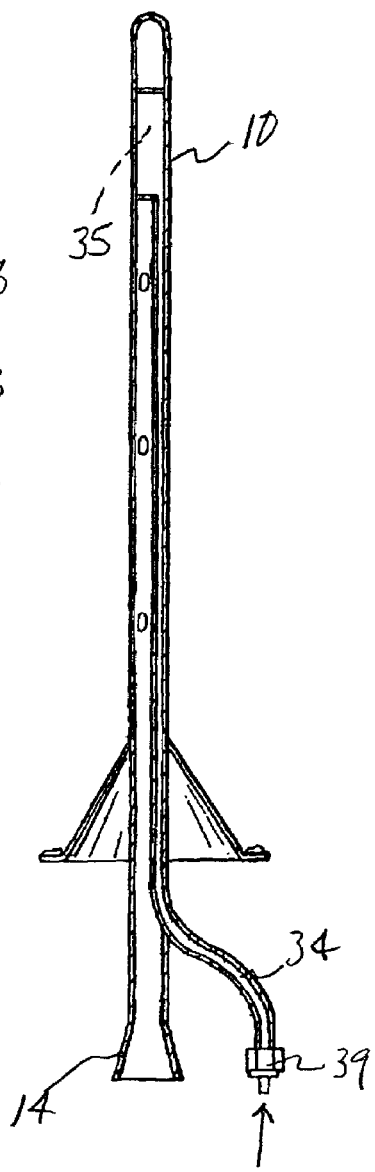

APPARATUS AND METHOD OF IDENTIFYING RECTOVAGINAL FISTULAS

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The method and apparatus of the present invention relates to rectovaginal fistulas. More particularly, the present invention relates to an apparatus and method for identifying the precise location of rectovaginal fistulas through the use of a dye or gel inserted into the rectum and forcing the dye or gel through the fistula and out into the vagina, whereby the fistulas can be visually located and treated.

2. General Background of the Invention

Rectovaginal fistulas, defined as a communication between the rectum and the vagina, is an undesirable physical abnormality, and can lead to serious health consequences. Under the present state of the art, the use of diagnostic modality such as barium enema, colonoscopy, MRI and ultrasound do not identify the specific location of a rectovaginal fistula. Many procedures are able to rule out a colovaginal fistula (communication between the colon and the vagina), but the precise location of a rectovaginal fistula can be elusive, and therefore continues to be a problem in the medical field.

A search has been conducted in the U.S. Patent and Trademark Office, and the patents located as a result of this search are submitted herewith in the prior art statement.

Therefore, there is a need in the art for a method and apparatus which provides a simple yet precise technique for locating rectovaginal fistulas, so that the physician may then repair the fistula at an early stage in its development, and avoid serious health consequences for the patient.

BRIEF SUMMARY OF THE INVENTION

The method and apparatus of the present invention solves the problems in the art in a simple and straightforward manner. What is provided is an apparatus for locating rectovaginal fistulas which includes a cannula (which would be equivalent to a Foley catheter of the type used to drain bladders) of a predetermined length, open-ended on is first end and having an inflatable balloon portion on its second end; the second end of the cannula being insertable into a patient's rectum; and the first end of the cannula further including a cone portion along its length to seal up against the exterior wall entrance to the rectum. There is further provided a channel within the interior of the cannula for inflating the balloon after the cannula is in place in the rectum to seal the rectum passage. Further, the cannula includes a plurality of spaced apart openings along its wall between the balloon and the first end of the cannula. There is then provided a fluid, such as air, soapy water or a colored gel insertable into the first end of the cannula to the extent that the gel or other fluid escapes the cannula through the openings and enters the void between the cannula and the wall of the rectum with sufficient gel entering the void so that gel would seep into any fistulas present and would be visually identifiable in the vagina for repair. The apparatus would further a funnel at the first end of the cannula for sealing against the exterior wall entrance to the rectum to avoid gel escaping through the rectal opening. There is further provided graduations at ten centimeters, 7.5 centimeters, 5 centimeters, and 2.5 cm along the wall of the cannula between the cone portion and the balloon portion for measuring the quantity of gel or other fluid being delivered.

The invention also includes the method of identifying the location of rectovaginal fistulas by providing a cannula having a first open end and a second closed end insertable into the rectum to a predetermined distance, while the first open end remaining exterior to the rectum. Next there is provided an inflatable balloon adjacent the second end of the cannula and a sealing cone at the first open end of the cannula; next there is provided a plurality of openings in the wall of the cannula between the balloon and the sealing cone, with the sealing cone sealing off the rectal opening between the cannula and the rectal wall; the balloon is then inflated against the wall of the rectum for preventing fluid to move beyond the position of the balloon in the rectum. Next, a dye containing gel or other fluid is inserted into the first open end of the cannula in sufficient quantity to allow the gel or other fluid to enter the rectal space and pass into any fistulas present between the balloon and the cone sealing the rectal opening so that a physician or the like may identify the precise location of the gel or other fluid entering the vagina through fistulas for ultimate treatment.

Therefore, it is a principal object of the present invention to provide a concise method and apparatus for identifying rectovaginal fistulas by the use of a dye containing gel or other fluid that is inserted into the rectal space and would seep through the fistulas for identification;

It is a further object of the present invention to provide an apparatus which can be easily inserted into the rectum and sealed on its first and second ends, so that a dye containing gel may be inserted into a passageway in the apparatus and seep into the rectal opening and ultimately through any fistula that may be present between the rectum and the vagina.

It is a further object of the present invention to provide an apparatus which allows a physician to precisely spot the location of fistulas between the rectum and the vagina by visually seeing gel seeping through the fistulas after the gel has been inserted into the rectum under a controlled method as defined in the invention.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 1 illustrates an overall view of the apparatus of the present invention;

FIG. 2 illustrates a cross section view of the preferred embodiment of the apparatus of the present invention;

FIG. 3 illustrates the cone portion of the apparatus of the present invention;

DETAILED DESCRIPTION OF THE INVENTION

Figure 4:
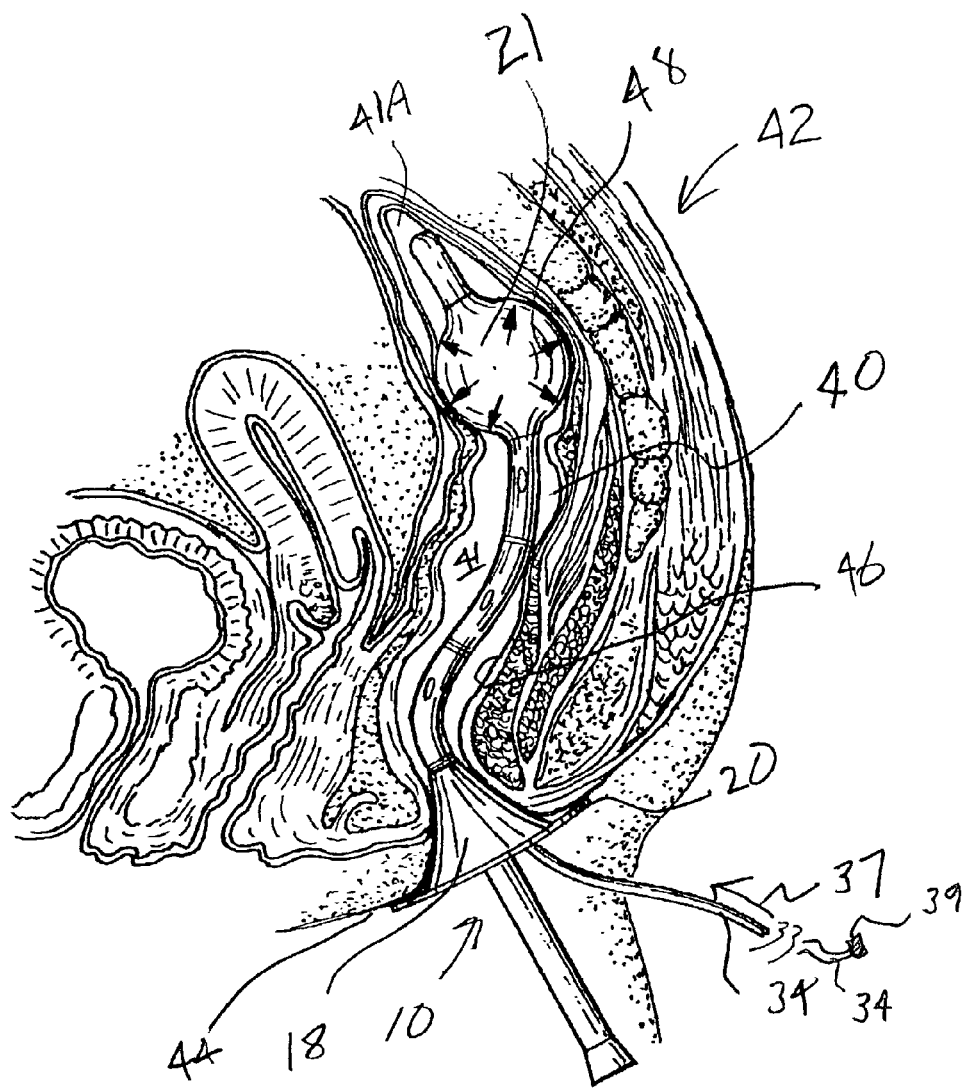
FIG. 4 illustrates the apparatus of the present invention sealingly positioned within the rectum of a patient.

FIGS. 1–6 illustrate the preferred embodiment of the apparatus and method of the present invention with the apparatus being identified by the numeral 10. As illustrated in full view in FIG. 1, apparatus 10 includes an elongated cannula portion 12 of a predetermined length in the neighborhood of 35 cm, having a first open end 14, with an opening 15, and a second closed rounded end 16. As illustrated, cannula 10 further comprises a cone member 18 positioned a distance down the length of cannula 10, preferably approximately 10 cm from the open end 14, the function of which will be described further. Cone 18 has a flat shoulder member 20 which will be utilized in a function to be described further. There is also noted an inflatable balloon portion 21, at the second end 16, the function also which will be identified later. As seen in FIG. 1, balloon portion 21 is shown in the deflated state, as illustrated. Further, there is illustrated along the length of cannula 10 a plurality of graduations, which represent particular distances along its length. For example, line 22 represents a distance of 2.5 cm proximal to the balloon; double line 23 represents 5 cm therefrom; triple line 24 represents 7.5 cm therefrom, and quadruple line 25 represents 10 cm therefrom. Also, there is illustrated a plurality of openings 28, 30 and 32 into each of the graduation lines, whereby a gel or the like substance, such as air or soapy water, will be excreted therefrom as will be described further. For purposes of brevity, the reference to gel in the specification does not limit the substance only to gel but is foreseen to include other fluids such as air, or soapy water or other substance that would be equivalent to gel. Each opening 28, 30 and 32 are in pairs, with the second opening of each pair positioned directly opposite the openings in the cannula wall 13 seen in FIG. 1.

As further seen in FIGS. 1 and 2, there is illustrated a tube member 34 which is positioned within the interior space 35 of cannula 10. As seen clearly in FIG. 2 in cross-section view, tube 34 extends into balloon 21, with the tube 34 serving as a means for introducing air or fluid into tube 34 which would have a direct communication with the interior of the balloon 21 for expanding the balloon as will be described further. The tube 34 would normally include a luer lock 39 for a syringe to be connectable thereto if needed.

FIG. 3 illustrates a partial view of the cone member 18 as it is secured to the wall 13 of the cannula 10 during use. It should be further noted that the cannula 10 on its first end 14 is in a funnel shape 17 in order to facilitate the introduction of gel or fluid into the interior space 35 of cannula 10 as will be described further.

Turning now to FIG. 4, FIG. 4 represents the second end 16 of apparatus 10 having been inserted into the rectum 40 of a patient 42. As seen, the cannula 10 has been inserted to the point where the wall 19 of the cone member 18 has made contact with the exterior portion of 44 of the patient's rectum. At that point, the shoulder 20 of the cone 18 would be sealed off using adhesive material, such as adhesive tape, so as not prevent passage of fluid or the like between the cone and the interior wall 46 of the rectum 40. Since the cannula 10 is a flexible tube, as is seen, it has flexed during its passage through the rectum 40, and it has been inserted through its entire length into the rectum. At that point, air or fluid is introduced into the tube 34 in the direction of arrow 37 through a syringe, for example, attached to the tube via a luer lock 39, which would inflate the balloon 21 as seen by the arrows 48. At that point, the balloon is fully inflated so that there can be no passage between the interior space 41 of the rectum 40 between the balloon 21 and the sealing cone 18 and that space 41A of the rectum on the distal side of the inflated balloon 21, after the balloon 21 has been inflated as seen in FIG. 4.

Figure 5:
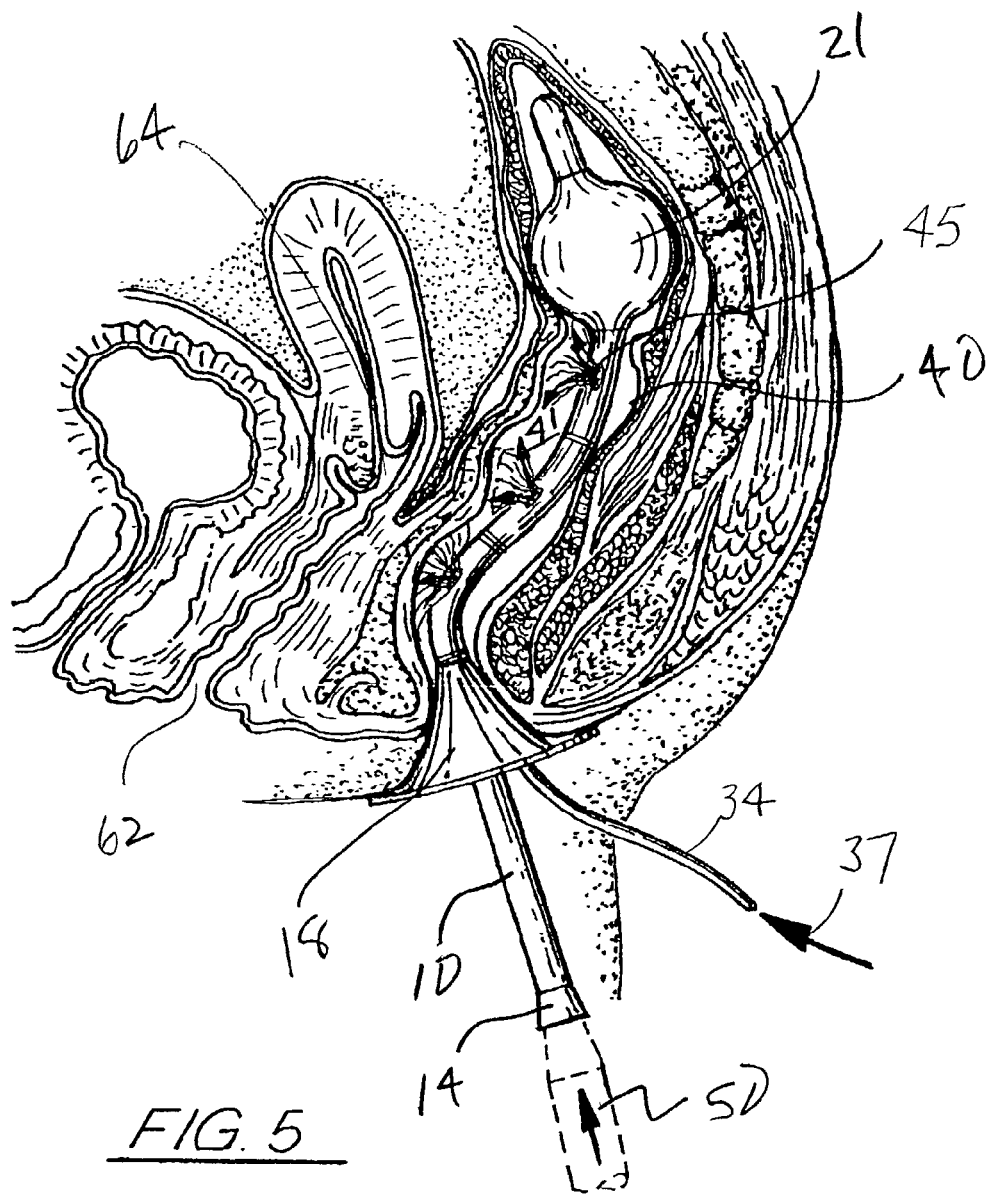
FIG. 5 illustrates the insertion of the dye containing gel or other fluid through the openings in the wall of the apparatus of the present invention during use.

After the cone 18 has been sealed, reference is now made to FIG. 5, where a gel introducing member 50 is placed at the funnel opening 14 of the cannula 10. At that point, a liquid gel 45, which may contain a dye or may be naturally a particular color, is then injected into the cannula space 13, arrow 52, and the cannula is filled with gel 45 to the point that the gel 45 begins to exit the openings 28, 30 and 32 in the cannula wall, and begin to fill the void space 41 within the rectum 40 as more and more gel is introduced. Because of the expanded balloon 21, the gel cannot pass the balloon as it fills the space 41 and cannot exit the rectum because of the sealing of the cone 18 as was described earlier.

Figure 6:
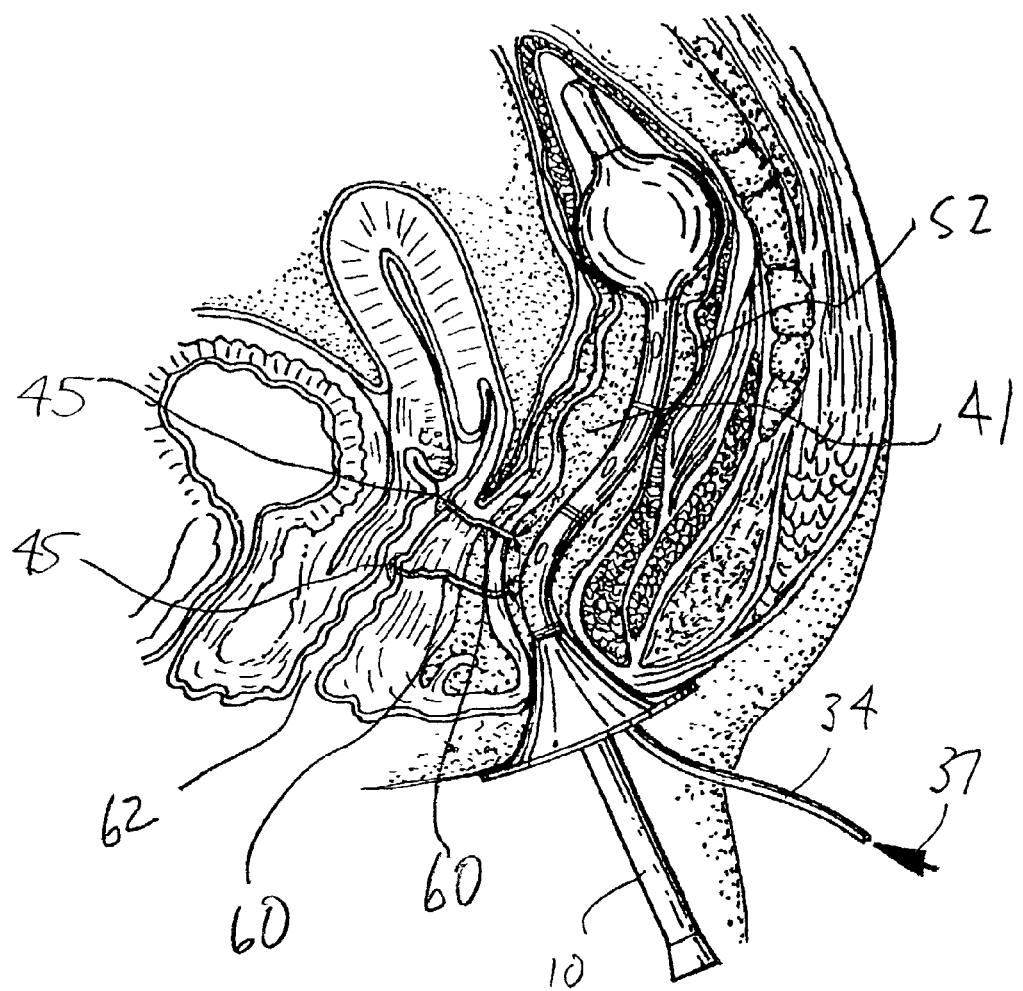
FIG. 6 illustrates the passage of the gel through fistulas which have occurred between the rectum and the vagina for ultimate location by the physician for repair.

Reference is now made to FIG. 6 where a sufficient quantity of gel 45 has filled the rectum space 41 so that the gel now seeping through a pair of fistulas 60 which are present, but could not be visually located by the physician. At this point, the physician is then able to view the gel through the vaginal opening 62 and see the gel 45 being extruded into the vagina 64 through the two fistulas 60, Therefore, the physician may induce treatment which will probably involve repairing each of the fistulas so as to avoid any further communication between the rectum 40 and the vagina 64. Of course, following the visual location of the fistulas 60, and treatment of same, the balloon 21 would be allowed to deflate, and the cannula 10 would simply be removed from the rectum 40, the gel 45 removed, and the patient would have undergone the necessary treatment.

The foregoing embodiments are presented by way of example only; the scope of the present invention is to be limited only by the following claims.

The invention claimed is:

1. An apparatus for locating rectovaginal fistulas, comprising:
   a. a main, flexible cannula of a predetermined length, having a cannula wall, a proximal end portion with a fluid inlet opening and a distal end portion, the distal end portion insertable a distance into the rectum of a patient, the proximal end portion having a generally conically shaped sealing member that is attached to the cannula wall, and positioned distally of the fluid inlet opening;
   b. an inflatable balloon on the distal end portion for sealing space between the cannula wall and the rectal wall;
   c. a second cannula connected to and generally aligned with the first cannula and having proximal and distal end portions, the distal end portion being in fluid communication with the balloon;
   d. a fitting on the proximal end of the second cannula for accepting a syringe for enabling inflation of the balloon via the second cannula;
   e. a plurality of openings provided along the wall of the first cannula in between the sealed first and second ends of the cannula;

f. a diagnostic fluid insertable into an opening at the first end of the main, flexible cannula and being of a volume sufficient to fill the cannula and exit through the openings and enter a void between the cannula and the wall of the rectum, with sufficient volume of fluid being provided entering the void so that the fluid would seep into any fistulas present and would be visually identifiable in the vagina for diagnosis and treatment.

2. The apparatus in claim 1, wherein the second cannula is sized and shaped for transporting air or water for inflating the balloon, and the fitting is a syringe lock.

3. The apparatus in claim 1, wherein the plurality of openings comprises three pairs of openings spaced along the wall of the main cannula for allowing the gel to escape from the cannula into the rectal space.

4. The apparatus in claim 1, wherein the cone member at the first end of the cannula is sealed against the exterior wall entrance to the rectum to avoid diagnostic fluid escaping through the rectal opening.

5. The apparatus in claim 1, wherein the distal end of the main cannula is closed and rounded for ease of insertion into the rectum.

6. The apparatus in claim 1, wherein the main cannula is graduated at 10 cm; 7.5 cm; 5 cm and 2.5 cm along its wall between the generally conically shaped portion and the balloon portion.

7. The apparatus in claim 1, wherein the proximal end of the main cannula has a funnel at the fluid inlet opening to facilitate inserting a diagnostic fluid thereinto.

8. The apparatus in claim 1, wherein the diagnostic fluid includes one of a colored gel, air, or soapy water fluid.

9. An apparatus for locating rectovaginal fistulas, comprising:
  a. a first cannula of a predetermined length, having a cannula wall surrounding a bore, proximal and distal end portion, and an inflatable balloon portion on its distal end and providing a fluid inlet opening on its proximal end;
  b. the distal end of the cannula insertable into a patient's rectum;
  c. the proximal end portion of the cannula further comprising a cone portion near the proximal end but positioned distally of the fluid inlet opening for sealing against the exterior wall entrance to a patient's rectum;
  d. a pumping device for inflating the balloon after the cannula is in place in the rectum to form a seal in between the cannula wall and the rectum passage; the pumping device including a second cannula next to the first cannula;
  e. a plurality of openings provided along the wall of the cannula in between the balloon and the cone portion;
  f. a volume of a colored diagnostic gel insertable into the cannula and of sufficient volume so that the gel escapes the cannula through the openings and enters the void between the cannula and the wall of the rectum, with a sufficient volume of gel entering the void so that gel would seep into any fistulas present and would be visually identifiable in the vagina for repair.

10. The apparatus in claim 9, wherein the second cannula has a syringe lock on the exterior proximal end.

11. The apparatus in claim 9, wherein the plurality of openings comprises three pairs of openings spaced along the wall of the first cannula for allowing the gel to escape from the first cannula into the rectal space.

12. The apparatus in claim 9, wherein the cone portion at the proximal end of the first cannula is sealed against the exterior wall entrance to the rectum to avoid gel escaping through the rectal opening.

13. The apparatus in claim 9, wherein the distal end of the first cannula is closed and rounded for ease of insertion into the rectum.

14. The apparatus in claim 9, wherein the first cannula is graduated at 10 cm; 7.5 cm; 5 cm and 2.5 cm along its wall between the cone portion and the balloon portion.

15. The apparatus in claim 9, wherein the proximal end of the first cannula has a funnel at the fluid inlet opening to facilitate inserting gel thereinto.

16. An apparatus for locating rectovaginal fistulas of a patient, comprising:
  a. a first cannula of a predetermined length, having cannula wall surrounding a bore, a closed distal end and an proximal open end that provides a first fluid inlet opening, the closed distal end insertable a distance into the rectum of a patient;
  b. an inflatable balloon carried on the closed distal end for sealing a space in between the cannula wall and the rectal wall of a patient;
  c. a tapered sealing device on the first cannula positioned distally of the first fluid inlet opening;
  d. a plurality of openings provided along the wall of the first cannula between the inflatable balloon and tapered sealing device closed end and open end of the cannula;
  e. a second cannula attached to the first cannula and having a cannula wall, proximal and distal ends, the proximal end having a second fluid inlet opening, the distal end being in fluid communication with the balloon, the proximal end being connectable to an inflating device at the second fluid inlet opening;
  f. a volume of diagnostic fluid insertable into an opening in the open end of the first cannula to the extent that the fluid can be transmitted via the first cannula through the openings and to enter a diagnostic void between the cannula and the wall of the rectum, with sufficient diagnostic fluid entering the void so that the diagnostic fluid would seep into any fistulas present and would be visually identifiable in the vagina for treatment; and
  g. an inflating device connectable to the second cannula at the second fluid inlet opening for inflating the balloon.

* * * * *